United States Patent [19]

Böhm et al.

[11] Patent Number: 5,276,218
[45] Date of Patent: Jan. 4, 1994

[54] PREPARATION OF β-FLUOROALCOHOLS

[75] Inventors: Stefan Böhm; Albrecht Marhold, both of Leverkusen; Dietmar Bielefeldt, Ratingen, all of Fed. Rep. of Germany

[73] Assignee: Bayer Aktiengesellschaft, Leverkusen, Fed. Rep. of Germany

[21] Appl. No.: 730,368

[22] Filed: Jul. 15, 1991

[30] Foreign Application Priority Data

Jul. 25, 1990 [DE] Fed. Rep. of Germany ....... 4023625

[51] Int. Cl.$^5$ ............................................. C07C 37/68
[52] U.S. Cl. .................................................. 568/842
[58] Field of Search ................................ 568/842, 841

[56] References Cited

PUBLICATIONS

Patent Abtracts of Japan, vol. 14, No. 431 (C-0759) (1990) & JP-A-21 67 240 (Nippon Mining Co. Ltd).
J. Chem. Soc. Commun. 1989 (1848)—I. Shahak et al.
Oshida et al, Tetrahedron Letters, 21, 1755-56, (1980).
Grieco et al, J. Org. Chem. 44, 2189-93 (1979).
Ichihara et al. J. Chem. Soc. Chem. Commun. 1848-50 (1989).
Landini et al, Tetrahedron Letters, 31, 7209-12, 1990.

Primary Examiner—Marianne M. Cintins
Assistant Examiner—Rebecca Cook
Attorney, Agent, or Firm—Sprung Horn Kramer & Woods

[57] ABSTRACT

Process for the preparation of β-fluoroalcohols of the formula (I)

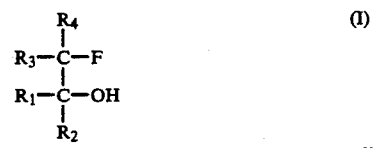

in which
 $R^1$ and $R^2$ represent straight-chain or branched alkyl and
 $R^3$ and $R^4$ represent hydrogen or alkyl,
in which epoxides of the formula (II)

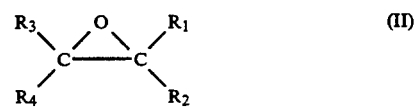

are reacted with sodium hydrogen fluoride or potassium hydrogen fluoride under pressure in the presence of diluents.

8 Claims, No Drawings

PREPARATION OF β-FLUOROALCOHOLS

The invention relates to a new process for the preparation of β-fluoroalcohols which are valuable intermediates for synthesis in organic chemistry. For example, they can be employed as precursors for the preparation of herbicides.

It is already known that the ring-opening fluorination of epoxides with fluorinating agents leads to β-fluoroalcohols (cf., for example, J. Chem. Soc. Chem. Comm. 1989, (1848)). The disadvantage of this method is that different stereoselectivities and regioselectivities are found, depending on the fluorination method. Due to side-reactions (for example polymerization), the yields are mostly unsatisfactory (J. Chem. Soc. C, 1968, 2129).

In the case of the simple aliphatic epoxides, only fluorination methods which operate at low temperatures were used to date such as, for example, hydrogen fluoride in certain solvents (J. Gew. Chem. (USSR), 19, 95 (1949)), HF/pyridine complexes (Isr. J. Chem. 17, 148 (1978) or HF/amine complexes (J. Org. Chem. 53, 1026 (1988)). The disadvantage of these methods is that, in the case of asymmetrical epoxides, products or mixtures of products are obtained in which the fluorine atom is predominantly, or exclusively, bonded to the higher-substituted C atom.

These methods therefore generally do not, or only with great difficulty, permit preparation of fluoroalcohols in which the fluorine atom is bonded to the lower-substituted C atom.

It is furthermore known that ethylene oxide can be reacted with bifluorides to give ethylene fluorohydrin (J. Gew. Chem. (USSR), 19, 95 (1949)). The disadvantage of this process are the low yields. Since ethylene oxide is a symmetrically substituted compound, the question of regioselectivity is of no importance.

It has now been found that β-fluoroalcohols of the formula (I)

$$\begin{array}{c} R_4 \\ | \\ R_3-C-F \\ | \\ R_1-C-OH \\ | \\ R_2 \end{array} \quad (I)$$

in which
$R^1$ and $R^2$ represent straight-chain or branched alkyl and
$R^3$ and $R^4$ independently of one another represent hydrogen or straight-chain or branched alkyl,
are obtained when epoxides of the formula (II)

$$\begin{array}{c} R_3 \diagdown \quad O \quad \diagup R_1 \\ \diagdown \diagup \diagdown \diagup \\ C\text{———}C \\ \diagup \qquad \diagdown \\ R_4 \qquad R_2 \end{array} \quad (II)$$

in which
$R^1$, $R^2$, $R^3$ and $R^4$ have the abovementioned meanings,
are reacted with potassium hydrogen fluoride (KHF$_2$) or sodium hydrogen fluoride (NaHF$_2$) under pressure in the presence of diluents.

It is surprising that the fluoroalcohols are obtained in such good yields under these drastic conditions since it is known that epoxides tend to undergo side-reactions which reduce the yield (J. Chem. Soc. C, 1968, 2129).

Moreover, it is surprising that a pronounced regioselectivity of the reaction is observed which is the opposite of the previously observed regioselectivities in the fluorination of simple aliphatic epoxides (Bull. Soc. Chim. France (1968) 2929). For example, using the new process, it is possible to obtain fluoro-tert.-butanol as the main product when isobutylene oxide is reacted with KHF$_2$, while the customary processes give an isomeric alcohol as the main product or single product.

Compared with other methods, the process is distinguished by a series of advantages. It can be carried out in a very simple fashion and using inexpensive starting materials and agents. Moreover, the altered regioselectivity allows access to compounds which are difficult to synthesize by other methods.

With the aid of the process according to the invention, β-fluoroalcohols which are preferably obtained are those of the formula (I) in which $R^1$ and $R^2$ independently of one another represent straight-chain or branched alkyl having 1 to 4 carbon atoms, particularly preferably methyl, ethyl, n- or iso-propyl, in particular methyl or ethyl, and $R^3$ and $R^4$ independently of one another represent hydrogen, straight-chain or branched alkyl having 1 to 4 carbon atoms, particularly preferably hydrogen, methyl or ethyl and, in particular, hydrogen.

If, for example, isobutylene oxide is used as the starting compound, the process according to the invention can be illustrated by the following equation:

$$\underset{\underset{CH_3}{|}}{H_2C}\overset{O}{\diagdown}\underset{}{\overset{CH_3}{\diagup}}C \xrightarrow[\text{under pressure}]{KHF_2}$$

$$\begin{array}{cc} CH_2F & CH_2OH \\ | & | \\ CH_3-C-OH & CH_3-C-F \\ | & | \\ CH_3 & CH_3 \end{array}$$

$$75:25$$

The epoxides of the formula (II) which are required for carrying out the process according to the invention are known.

For carrying out the process according to the invention, equivalent amounts of epoxide of the formula (II) and of the fluorinating agent are generally reacted, or the fluorinating agent is employed in excess.

It is preferred to employ the sodium hydrogen fluoride or potassium hydrogen fluoride in excess in an amount of 1.01 to 1.5 equivalents, particularly preferably in an amount of 1.05 to 1.3 equivalents.

When carrying out the process according to the invention, the reaction temperatures can be varied within a substantial range. In general, the process is carried out at temperatures between 80° C. to 300° C., preferably between 110° C. and 180° C.

The process according to the invention is carried out in closed apparatuses under pressure. The pressure can be varied by forcing in an inert gas within wide limits. It is preferred to carry out the process at pressures from 1 to 20 bar.

The reaction according to the invention can be carried out continuously or batchwise.

In general, it is advantageous to carry out the process according to the invention in the presence of a solvent.

Suitable solvents are those which are inert or substantially inert under the reaction conditions. Possible examples are ethers, for example ethyl propyl ether, n-butyl ether, di-n-butyl ether, diisobutyl ether, diisoamyl ether, diisopropyl ether, anisole, phenetole, cyclohexyl methyl ether, diethyl ether, tetrahydrofuran, dioxane, thioanisole, β,β'-dichlorodiethyl ether; polyethylene glycol ethers such as ethylene glycol dimethyl ether, ethylene glycol diethyl ether, ethylene glycol di-n-propyl ether, ethylene glycol diisopropyl ether, ethylene glycol di-n-butyl ether, ethylene glycol diisobutyl ether, ethylene glycol di-sec.-butyl ether, ethylene glycol di-tert.-butyl ether, diethylene glycol dimethyl ether, diethylene glycol diethyl ether, diethylene glycol di-n-propyl ether, diethylene glycol diisopropyl ether, diethylene glycol di-sec.-butyl ether, diethylene glycol di-tert.-butyl ether; analogous diethers of triethylene glycol and of tetraethylene glycol; diethylene glycol monomethyl ether, diethylene glycol monoethyl ether, triethylene glycol monobutyl ether, ethylene glycol, diethylene glycol, triethylene glycol, tetraethylene glycol, 1,2-propanediol, 1,3-propanediol; sulphoxides such as dimethyl sulphoxide, diethyl sulphoxide, dimethyl sulphone, diethyl sulphone, methyl ethyl sulphine, tetramethylene sulphone (sulpholane); N-methylpyrrolidone, dimethylformamide, hexamethylphosphoric triamide, N,N'-dimethylpropyleneurea, N-methylcaprolactam; benzene, toluene; acetonitrile, and desired mixtures of these solvents as regards quality and quantity.

Preferred solvents are diethylene glycol, triethylene glycol, tetraethylene glycol, higher glycols, if appropriate as a mixture, and also N-methylpyrrolidone; glycols are particularly preferred. Any desired amounts of solvent can be used relative to the starting compound of the formula (II). An example of a suitable amount of solvent is such an amount that a 10 to 80% by weight mixture of the starting compound is present in the particular solvent or solvent mixture. The concentration of the epoxide in this mixture is preferably 35–65% by weight.

The reaction can also be carried out in the presence of catalysts, for example crown ethers. In general, they affect the reaction of the starting compounds and the yields only slightly.

The reaction mixture is worked up by distillation, by distilling off the product or product mixture from the solvent and the salts at pressures between 10 mbar and atmospheric pressure, and, if appropriate, purification or separation by a redistillation.

The process according to the invention is illustrated by the examples which follow.

EXAMPLE 1

Reaction of isobutylene oxide with potassium hydrogen fluoride

A mixture of 2.7 kg (34.6 mol) of potassium hydrogen fluoride and 3 l of tetraethylene glycol is initially introduced into an autoclave and heated to 150° C. 2 kg (28.2 mol) of isobutylene oxide are pumped in in the course of 4 hours. This is followed by subsequent stirring for 4 hours at 150° C. After cooling and letting down the pressure, the product is removed from the reaction mixture by distillation under reduced pressure. 1.64 kg (63%) of crude product are obtained which, according to GC and NMR spectra, contain 75% of fluoro-tert.-butanol (1-fluoro-2-methyl-propan-2-ol) and 25% of the isomeric fluoroalcohol 2-fluoro-2-methyl-propan-1-ol. Pure fluoro-tert.-butanol can be obtained by fractional distillation.

EXAMPLE 2

Reaction of cis-2,3-butene oxide with potassium hydrogen fluoride

The reaction is carried out analogously to Example 1. 3-Fluoro-butan-2-ol is obtained in 59% yield as a stereochemically uniform compound (racemate of R,R and S,S configuration.

EXAMPLE 3

Reaction of 1,2-butene oxide with potassium hydrogen fluoride

The reaction is carried out analogously to Example 1. A mixture of 1-fluoro-butan-2-ol (70%) and 2-fluoro-butan-1-ol (30%) is obtained in 69% yield.

The β-fluoroalcohols of the formula (I) which can be prepared by the process according to the invention are valuable starting substances for the synthesis of biologically active compounds such as, for example, for the synthesis of substituted triazolinones (cf. EP-A 294,666), which have good herbicidal properties).

For example, by reacting β-fluoroalcohols of the formula (I) with hydrogen cyanide or aryl cyanides or alkyl cyanides, in particular hydrogen cyanide, in the presence of sulphuric acid and if appropriate in the presence of a diluent such as, for example, dioxane, at temperatures between 10° and 120° C., preferably 40° and 80° C., β-fluoro-tert.-alkylamides of the formula (III)

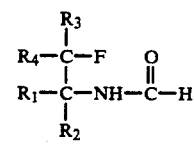

or

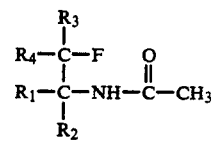

are obtained which, if appropriate after intermediate isolation, are hydrolyzed to give the β-fluoro-tert.alkylamine hydrochlorides of the formula (IV)

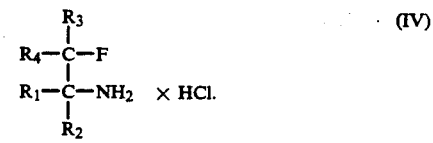

From the amine hydrochlorides of the formula (IV) or the free amines, isocyanates are obtained by reaction with phosgene, if appropriate in the presence of a diluent such as, for example, o-dichlorobenzene, if appropriate in the presence of a base such as, for example, triethylamine, and these isocyanates can then be reacted according to the processes described in EP-A 294,666 to give herbicidally active compounds.

Example for the preparation of

β-Monofluoro-tert.-butyl isocyanate:

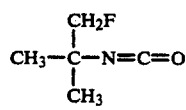

20 g (0.156 mol) of N-(fluoro-tert.-butyl)-amino hydrochloride are dissolved in 100 ml of o-dichlorobenzene. 45 g (0.5 mol) of phosgene are passed in at 140° C. After the excess phosgene has been expelled with nitrogen, the mixture is fractionated in vacuo.

9.5 g (52% of theory) of β-monofluoro-tert.-butyl isocyanate of melting point 110°-112° C. are obtained.

N-(Fluoro-tert.-butyl)amine hydrochloride:

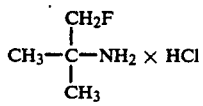

119 g (1 mol) of N-(fluoro-tert.-butyl)-formamide are treated with 1,000 ml of 20% strength hydrochloric acid, and the mixture is stirred for 4 hours at 70° C. The mixture is subsequently distilled under reduced pressure to dryness, and the residue is dried in vacuo to constant weight.

Yield: 120 g (94% of theory)
Melting point: 250° C.

N-(Fluoro-tert.-butyl)-formamide

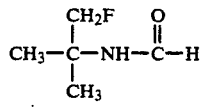

92 g (1 mol) of 1-fluoro-2-methyl-propan-2-ol (cf. Example 1 of the present application) are dissolved in 80 ml (2 mol) of hydrocyanic acid at 10° to 15° C. 140 g (1.4 mol) of concentrated sulphuric acid are slowly added dropwise with stirring. Subsequent stirring is then effected for 15 hours at room temperature.

Excess hydrocyanic acid is stripped off in vacuo, the residue is poured into 250 ml of ice-water, and the mixture is extracted 5 times using 100 ml of dichloromethane. After the extract has been dried with magnesium sulphate, the solvent is distilled off in vacuo.

| Yield: | 86 g | (72% of theory) |
|---|---|---|
| Boiling point: | 53-54° C. | (0.05 mbar) |
| Purity: | 95% | (gas chromatography). |

It will be understood that the specification and examples are illustrative but not limitative of the present invention and that other embodiments within the spirit and scope of the invention will suggest themselves to those skilled in the art.

What is claimed is:

1. A process for the preparation of a β-fluoroalcohol of the formula

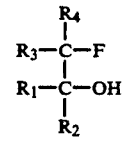

in which
$R_1$ and $R_2$ represent straight-chain or branched alkyl having 1 to 4 carbon atoms and
$R_3$ and $R_4$ independently of one another represent hydrogen or straight-chain or branched alkyl having 1 to 4 carbon atoms,
which comprises reacting an epoxide of the formula

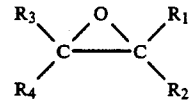

with a fluorinating agent consisting of sodium hydrogen fluoride or potassium hydrogen fluoride under pressure in the presence of a diluent.

2. The process according to claim 1, wherein $R^1$ and $R^2$ independently of one another represent methyl, ethyl or n- or iso-propyl.

3. The process according to claim 1, wherein $R^3$ and $R^4$ independently of one another represent hydrogen, methyl or ethyl.

4. The process according to claim 1, wherein $R^1$ and $R^2$ represent methyl and $R^3$ and $R^4$ represent hydrogen.

5. The process according to claim 1, wherein the reaction is carried out at a temperature between about 80° C. and 300° C.

6. The process according to claim 1, wherein about 1 to 1.5 equivalents of sodium hydrogen fluoride or potassium hydrogen fluoride are employed per equivalent of epoxide of the formula (II).

7. The process according claim 1, wherein about 1.05 to 1.3 equivalents of sodium hydrogen fluoride or potassium hydrogen fluoride are employed per equivalent of epoxide of the formula (II).

8. The process according to claim 4, wherein the reaction is carried out at a temperature between about 80° C. and 300° C., and about 1.05 to 1.3 equivalents of sodium hydrogen fluoride or potassium hydrogen fluoride are employed per equivalent of epoxide of the formula (II).

* * * * *